United States Patent [19]

Mennen

[11] 3,954,563
[45] May 4, 1976

[54] **APPARATUS ESPECIALLY USEFUL FOR DETECTION OF *NEISSERIA GONORRHOEAE* AND THE LIKE IN FEMALES**

[76] Inventor: Frederick C. Mennen, 506 Clay St., La Porte, Ind. 46350

[22] Filed: Mar. 28, 1975

[21] Appl. No.: 563,300

Related U.S. Application Data

[63] Continuation-in-part of Ser. No. 193,739, Oct. 29, 1971, Pat. No. 3,876,503.

[52] U.S. Cl. .............................................. 195/127
[51] Int. Cl.² ......................................... C12K 1/00
[58] Field of Search ............ 195/127, 139, 103.5 R; 23/253 TP

[56] References Cited
UNITED STATES PATENTS

| | | | |
|---|---|---|---|
| 3,446,596 | 5/1969 | Salivar et al. | 23/253 TP |
| 3,890,954 | 6/1975 | Greenspan | 195/139 |

*Primary Examiner*—Alvin E. Tanenholtz
*Attorney, Agent, or Firm*—Abraham A. Saffitz

[57] ABSTRACT

An apparatus for use in detecting *Neisseria gonorrhoeae* in females including a container and operative elements sealed therein. The test makes use of a dry pledget impregnated with reactant chemicals that is adapted to be activated upon being wetted. The test kit includes a stem fitted with an end swab upon which a specimen is collected by probing the patient, a reaction chamber cooperatively arranged with respect to the swab, and a frangible container for holding a wetting fluid adapted to activate the pledget when the test is to be run. The reaction chamber serves the dual function of providing a protective cover for the swab as the specimen is being collected thereon as well as holding the pledget in position for engagement with the specimen to complete the test. A protective skirt surrounds the stem above the swab to ensure the accuracy of the test by preventing such bacteria as pseudomonas which are also present in areas near where the specimen is collected.

1 Claim, 5 Drawing Figures

APPARATUS ESPECIALLY USEFUL FOR DETECTION OF NEISSERIA GONORRHOEAE AND THE LIKE IN FEMALES

CROSS-REFERENCE TO RELATED APPLICATIONS

This application is a continuation-in-part of my copending application Ser. No. 193,739, filed Oct. 29, 1971, entitled METHOD AND INSTRUMENT FOR THE DETECTION OF NEISSERIA GONORRHEAE WITHOUT CULTURE, now U.S. Pat. No. 3,876,503, issued Apr. 8, 1975. This parent application is specifically incorporated by reference herein.

Copending application, Ser. No. 537,593, filed Dec. 30, 1974 as a divisional under 37 CFR 1.60 of Ser. No. 193,739, entitled METHOD AND INSTRUMENT FOR THE DETECTION OF NEISSERIA GONORRHEAE WITHOUT CULTURE.

Copending application, Ser. No. 561,707 filed on even date herewith, 3/25/75 entitled AN INSTRUMENT FOR THE DETECTION OF NEISSERIA GONORRHOEAE AND THE LIKE.

BACKGROUND OF THE INVENTION

1. Field of the Invention
a. Present Status of the Problem

It is common knowledge that this country and most of the world is undergoing a veneral disease epidemic. In the United States along the disease has reached pandemic proportions. It is estimated that only one-fifth of the cases are reported and only one-third reach the attention of physicians and Public Health authorities in order to receive treatment. The availability of a simple, rapid and inexpensive test would aid in recognition and control of this disease.

The usual clinical evidence of a gonorrheae infection in the male is a purulent discharge from the meatus and urethra of the penis and a discharge in the ureal area of the female. As routine procedure, it is necessary to make a differential diagnosis of the nature of the discharge before antibiotics can be prescribed. As a rule the first test is to determine if the urethritis is gonococcal or non-specific in nature.

2. Summary of the Prior Art

While some prior art, U.S. Pat. No. 3,450,129, Avery et al., makes use of frangible ampuls for carrying reagents, the use of that method is directed specifically to transporting a living bacterial specimen to a laboratory for culture and using their apparatus and method for the purpose of preserving the viability of the bacteria until they can be cultured, the purpose is to provide a concentration of micro-organism, whereas this invention is a diagnostic one-use disposable test system and does not require culture. It is a direct test on the few organisms present in the urethral tract picked up on a sterile swab inserted therein. Diagnosis is made at the time of collection of the specimen.

OBJECTS OF THE INVENTION

An object of this invention is therefore to provide a disposable device and system which will operate directly on the female patient and give the clinician or physician a diagnostic tool which is time saving, inexpensive, and reliable.

A further object of the invention is to provide an instrument which tests and kills the organism by reason of the toxicity of the testing reagent yet is disposed of easily without bringing into contact with the hands of the clinician or physician with the discharge of the patient.

Still a further object of the invention is to provide a capped easily disposable one-use diagnostic instrument for testing Neisseria gonorrhoeae.

Still another object of the invention is to provide disposable device for sampling and collecting a specimen directly from the cervical area of a female patient in which a relatively thin swab and the end of the sampling stem is protected by a protective skirt which surrounds the stem and is placed above the swab, whereby interfering micro-organisms, such as pseudomonas, which are present in the area adjacent the sampling area, will be collected on the skirt rather than on the swab.

Still another object is to provide a thin elongated sampling swab adapted by its size and form to probe the cervical area and collect the sample effectively while being incontaminated by pseudomonas by virtue of the protective skirt which is also present.

SUMMARY OF THE INVENTION

The invention disclosed herein provides an improved disposable testing device for use with the procedure disclosed in the parent application Ser. No. 193,739, filed Oct. 29, 1971, now U.S. Pat. No. 3,876,503, issued Apr. 8, 1975 and includes a method for making use of this improved device after which it may be disposed of in a hygenic manner.

The principal object of this invention is to provide a diagnostic apparatus that may be conveniently used to detect Neisseria gonorrhoeae without making use of a culture or the classical gram-staining method, both of which are time consuming and expensive to perform and require trained technicians and laboratory equipment.

The present invention involves the use of a reagent such as an oxidase testing reagent as disclosed in the application Ser. No. 193,739. In the following the teaching of that invention, a pledget or carrier of any suitable material such as dacron fiber, cotton fiber or other porous material is impregnated or saturated with one of the disclosed reagents and then dried. It remains in the dry state until it is activated by a wetting agent.

The pledget is the principal component of the diagnostic system, as it contains the reactive chemical that is capable of identifying the gonococcus. In the dry state the oxidase reagent impregnated in the pledget will remain stable and is capable of long shelf life. The second part of the system is the wetting agent which is separated from the pledget by virtue of being contained in a frangible ampul. When the frangible ampul is crushed, the wetting agent contained therein is released, cativating the reagent in the pledget. The pledget after thus being sensitized is brought into contact with the specimen on the tip of the collecting swab, reacting with the gonococci present, causing the specimen located on the swab to take on a characteristic color depending on the choice of reagent used. The pledget being white or nearly colorless in appearance does not cause any confusion during the test because it does not react colorimetrically. The color change takes place on the specimen collected on the swab. The reaction time to indicate a positive specimen usually falls within the range of from 30 to 120 seconds.

As a screening test for gonorrheae in public V-D clinics, hospitals, physicians' offices and the Armed Forces, the present device serves as an inexpensive and accurate differential diagnostic aid to assist the physician or clinic in the choice of drug treatment. The need for a simple and inexpensive diagnostic system that can function in the field, independent of bacteriological and microscopic tests, is therefore well established. A method for such a test and an instrument for performing such a test is disclosed in my application Ser. No. 193,739, filed Oct. 29, 1971, entitled Method and Instrument for the Detection of Neisseria Gonorrheae without Culture and in the 37 CFR 1.60 divisional application Ser. No. 537,593, filed Dec. 30, 1974.

BRIEF DESCRIPTION OF THE DRAWING

In order to illustrate more fully the manner in which this improved instrument is used and its structure, reference is made to the drawing wherein.

DESCRIPTION OF THE PREFERRED EMBODIMENT(S)

Figures 1, 2, 3, 4, 5:
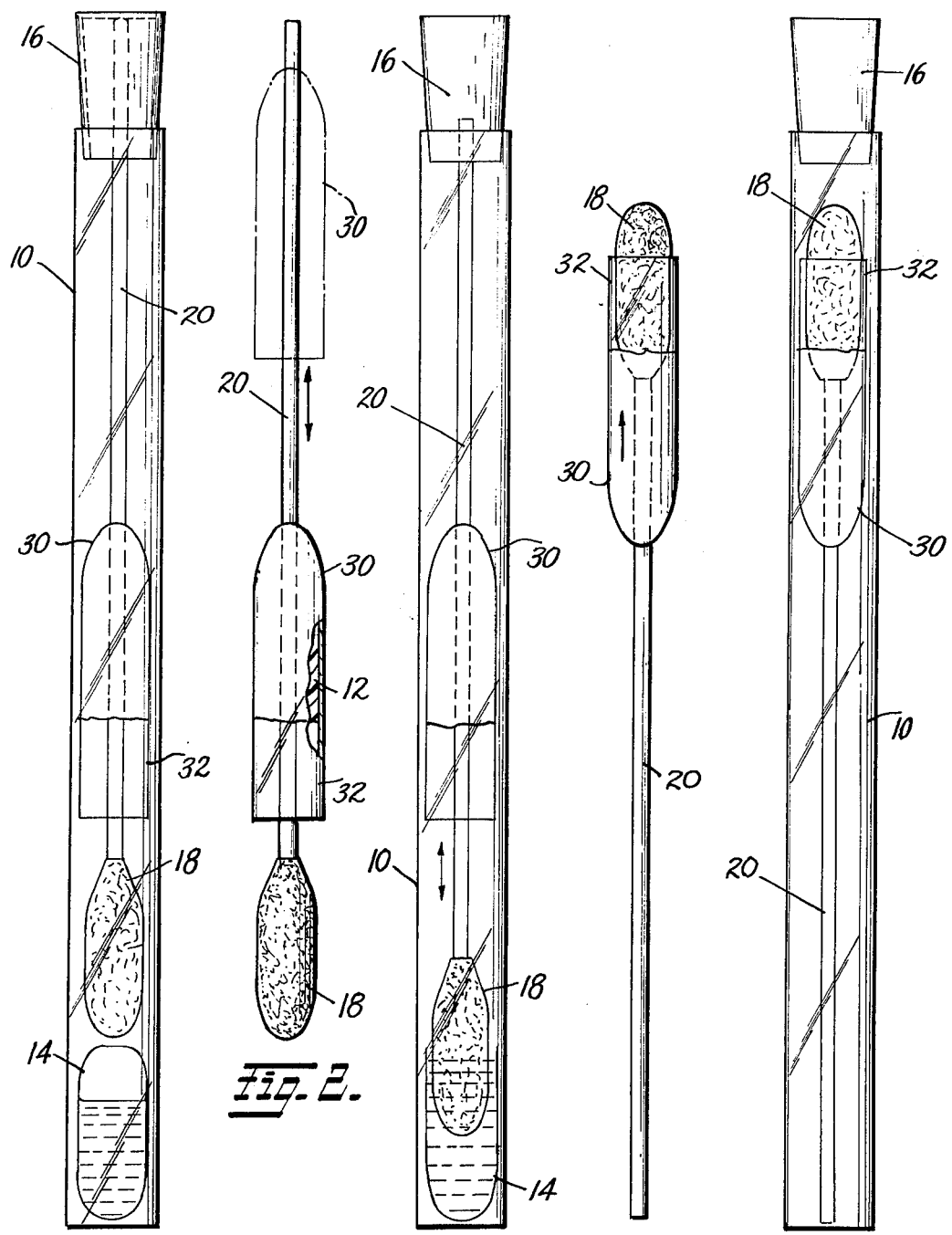
FIG. 1 is an elevational view of a disposable package including diagnostic reagent units for the rapid detection of Neisseria Gonorrheae.
FIG. 2 is an elevational view of the swab and reagent chamber removed from the package prior to obtaining a specimen.
FIG. 3 is an elevational view, showing the swab with a specimen thereon and the reagent chamber replaced in the package and fracturing the ampul containing the wetting agent.
FIG. 4 is an elevational view of the reaction chamber with the reaction material therein being pushed up against the swab; and, FIG. 5 is an elevational view of the disposable package with the swab and reaction chamber replaced showing the reaction taking place by the appearance of a color change in the specimen.

Referring more specifically to the drawing, which represents a perferred type of instrument capable of performing my test procedure on females, numeral 10 indicates a tube of transparent, rigid plastic, into which is inserted a pledget 12 of cotton impregnated or saturated with the oxidase reagent and dried. The pledget is seated in a reaction chamber 30 that is formed of transparent inert plastic, in the form of a bullet shape. The chamber 30 is slidably mounted on the handle 20 for swab 18, the reaction chamber having an extending skirt portion 32 that is adapted to surround the sides of the swab as best seen in FIGS. 4 and 5.

A frangible glass ampul 14 is disposed in the closed end of the tube 10 and a cap 16 is placed over the open end of the tube, sterile swab 18 with a plastic handle 20 to be used in obtaining a specimen of exudate is placed in the tube between the cap and the ampul. The ampul 14 contains a suitable wetting agent, as described in application Ser. No. 193,739 and is sufficiently frangible that it can readily be broken when the swab is pressed downwardly against its upper end whereupon the ampul shatters and permits its fluid contents to wet the swab as shown in FIG. 4. After the swab with a specimen thereon has been inserted in tube 10 and the swab is wetted upon breaking ampul 14, the capped container is put into an incubator for 15 minutes at 37°C. After the device is removed from the incubator, the swab is withdrawn from tube 10 and reaction chamber 30 is slid along handle 20 to place the wet swab in contact with the pledget as shown in FIG. 4. After the reaction chamber has been slid to the end of the handle 20 the assembly is returned to the tube 10 with the swab next to the open end of the tube and then the cap 16 is replaced while the test reaction proceeds. When the swab containing the specimen contacts the pledget, the impregnated oxidase reagent is activated and the reaction between the specimen on the swab and the reagent in the pledget commences immediately and, if gonicocci are present, the specimen on the swab changes color, normally to purple, red-orange, or dark gray, depending upon the reagent used in the pledget, thus indicating a positive test. The reaction is readily observed through the transparent tube 10 and the time to indicate a positive specimen usually falls within the range of from 30 to 120 seconds.

When a diagnostic test for gonorrheae is to be made, the package is opened and the sterile swab is removed from tube 10 and the reaction chamber is adjusted on handle 20 so that skirt 32 covers the sides of the approximately ½ inches cylindrically shaped swab. The swab is then inserted in the females vagina to be pushed into direct contact with her cervix to obtain a specimen on the end of the swab while the sides are protected from contact with any other portion of the vagina to avoid picking up a psuedomonas organism which might be present and produce a false reading on the test. The swab is then inserted, tip first, into the tube and the cap is then replaced. The swab is then pressed against the ampul, breaking same and releasing its contents.

The wetted swab and the reaction chamber are then removed from the tube and inserted as shown in FIG. 4. Then the reaction chamber is moved upwardly to move the pledget into direct contact with the specimen containing swab. This action also forces the skirt 32 to more fully surround the swab. The swab and reaction chamber unit is then replaced in tube 10 as above explained while the test proceeds. The specimen on the swab turning purple within 2 minutes is a positive test for gonorrheae. The use of this test gives the physician or clinician a rapid and accurate diagnostic tool in the first step of this differential diagnosis. After the test has been completed the entire instrument may be disposed of in any sanitary way such as by incineration.

The protective skirt 32 surrounding the swab 18 ensures the accuracy of the test by preventing the pickup of psuedomonas specimens that could give false results in this test. It is important therefore in taking a sample specimen from a female to ensure that the swab be carefully inserted into the vaginal cavity and that the swab have contact only with the cervix from which the desired specimen for the present test must be collected. The skirt 32 further protects the person performing the test from possible exposure to the specimen collected on the swab when the reaction chamber is slid along handle 20 after wetting of the swab, as is evident from the inspection of FIGS. 4 and 5.

The structure and operation of the method of using this instrument have been set forth above. While this description covers the preferred form of my invention, it is possible that modifications thereof may occur to those skilled in the art that will fall within the scope of the following claims.

What I claim is:

1. An instrument for use in the rapid detection of Neisseria gonorrhoeae without gram-staining and without culture comprising:
   an elongated rigid transparent tube;
   said tube being destructible by incineration;

said tube being closed at one end and open at the other end;

a replaceable cover for the open end of the tube;

said tube containing a frangible ampul holding a wetting fluid for activating an oxidase indicating reagent stored therein at the closed end of the tube;

a combined swab and handle therefore with a reaction chamber slidably mounted on said handle, said swab and handle being disposed in said container between the cap and said ampul;

said reaction chamber including a dry pledget impregnated with an oxidase indicating reagent;

said swab comprising a substantially cylindrical body in the range of one-half inch in diameter and one-half inch in length and said reaction chamber including a housing for said pledget and an extension skirt to receive the swab to place the swab and pledget in contact;

the exposed end of said swab being adapted to be engaged against the cervix of a female patient to obtain a test sample while said skirt protects the side walls thereof against contact with other surfaces in the vaginal cavity; and said swab at the end of its handle being adapted to be pressed against the frangible ampul when the cap is pressed on the tube to free the wetting fluid for wetting the swab, and said reaction chamber being movable on the handle of the swab to place the pledget in contact with the wetted swab to activate the oxidase indicating reagent whereby to make a preliminary test of the specimen to determine whether Neisseria Gonorrhoeae is present by noting a color change on the swab when such is the case, whereupon the assembled instrument and its contents may be safely disposed of.

\* \* \* \* \*